United States Patent [19]
Bormann et al.

[11] Patent Number: 5,536,413
[45] Date of Patent: Jul. 16, 1996

[54] METHOD FOR TREATING A PARENTERAL EMULSION-CONTAINING MEDICAMENT FLUID

[75] Inventors: Thomas J. Bormann, Melville; Thomas C. Gsell; Vlado I. Matkovich, both of Glen Cove; Gerard R. Del Giacco, Yonkers, all of N.Y.

[73] Assignee: Pall Corporation, East Hills, N.Y.

[21] Appl. No.: 875,774

[22] Filed: Apr. 29, 1992

Related U.S. Application Data

[63] Continuation-in-part of Ser. No. 620,775, Dec. 3, 1990, Pat. No. 5,252,222.

[51] Int. Cl.$^6$ .......................... B01D 39/00; B01D 61/00
[52] U.S. Cl. .......................... 210/650; 210/436; 210/472; 210/651; 210/767; 422/1
[58] Field of Search .................................... 210/641, 650, 210/651, 653, 654, 188, 321.64, 767, 321.84, 435, 436, 472, 489, 492, 500.42, 500.38, 500.23; 604/405, 406; 422/1, 101; 436/177, 178; 55/421; 95/241; 96/155

[56] References Cited

U.S. PATENT DOCUMENTS

| | | | |
|---|---|---|---|
| 3,246,767 | 4/1966 | Pall et al. | 210/505 |
| 3,353,682 | 11/1967 | Pall et al. | 210/505 |
| 3,592,245 | 7/1971 | Schneller et al. | |
| 3,803,810 | 4/1974 | Rosenberg | 55/482 |
| 4,203,848 | 5/1980 | Grandine, II | 210/490 |
| 4,340,479 | 7/1982 | Pall | 210/490 |
| 4,568,366 | 2/1986 | Frederick et al. | 210/436 |
| 4,617,124 | 10/1986 | Pall et al. | 210/638 |
| 4,618,533 | 10/1986 | Steuck | 428/315.7 |
| 4,701,267 | 10/1987 | Watanabe et al. | 210/806 |
| 4,702,840 | 10/1987 | Degen et al. | 210/638 |
| 4,707,266 | 11/1987 | Degen et al. | 210/638 |
| 4,774,132 | 9/1988 | Joffee et al. | 428/290 |
| 4,798,676 | 1/1989 | Matkovich | 210/767 |
| 4,855,163 | 8/1989 | Joffee et al. | 427/244 |
| 4,886,836 | 12/1989 | Gsell et al. | 521/53 |
| 4,906,374 | 3/1990 | Gsell | 210/490 |
| 4,915,839 | 4/1990 | Marinaccio et al. | 210/500.23 |
| 4,925,572 | 5/1990 | Pall | 210/767 |
| 4,954,256 | 9/1990 | Degen et al. | 210/490 |
| 4,964,989 | 10/1990 | Gsell | 210/490 |
| 5,019,260 | 5/1991 | Gsell et al. | 210/490 |
| 5,105,993 | 4/1992 | La Haye et al. | 210/321.89 |
| 5,126,054 | 6/1992 | Matkovich | 210/641 |
| 5,252,222 | 10/1993 | Matkovich et al. | 210/650 |

FOREIGN PATENT DOCUMENTS

WO9117809  11/1991  WIPO.

OTHER PUBLICATIONS

Rueter, "CDC Raps Handling of Anesthetic", The Washington Post, Jul. 20, 1995, p. A4.
"Postoperative Infections at Texas Hospital Prompt Drug Warning" Texas Medicine, vol. 86, No. 9, Sep. 1990, p. 58.
"Postsurgical Infections . . . Maine, & Michigan, 1990", MMWR, vol. 39, No. 25, Jun. 29, 1990, pp. 426–433.
Diprivan® (Propofol) Professional Information Brochure, "Emulsion For IV Administration", Feb. 1991.
Deitel, "Total Nutrient Admixtures . . . ", Oct. Dec., 1987, Jan. 1988.
Driscoll, "Clinical Issues . . . Nitrient Admixtures", DICP, The Annals of Pharmacology, vol. 24, Mar. 1990, pp. 296–303.
Rubin et al, "Use of 5–Micron . . . Parenteral Nutrition", Clinical Nutrition, No. 4, 1985, pp. 163–168.
Levchuk et al, "Method for Testing . . . Nutrient Admixtures", Amercan Journal of Hospital Pharmacy, vol. 45, pp. 1311–1121, 1988.
D'Angio et al, "The Growth of Mircoorganisms . . . Admixtures", Journal of Parenteral . . . Nutrition, vol. 11, No. 4, 1987, pp. 394–397.

*Primary Examiner*—John Kim
*Attorney, Agent, or Firm*—Leydig, Voit & Mayer

[57] ABSTRACT

Processes and systems are provided for treating parenteral emulsion-containing medicament fluids are provided.

23 Claims, 4 Drawing Sheets

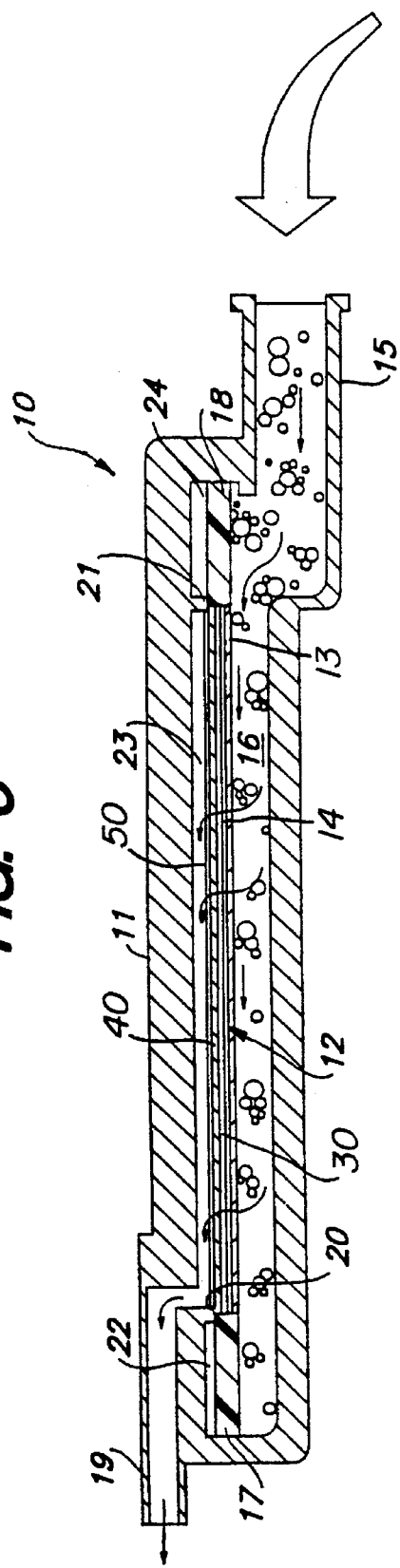
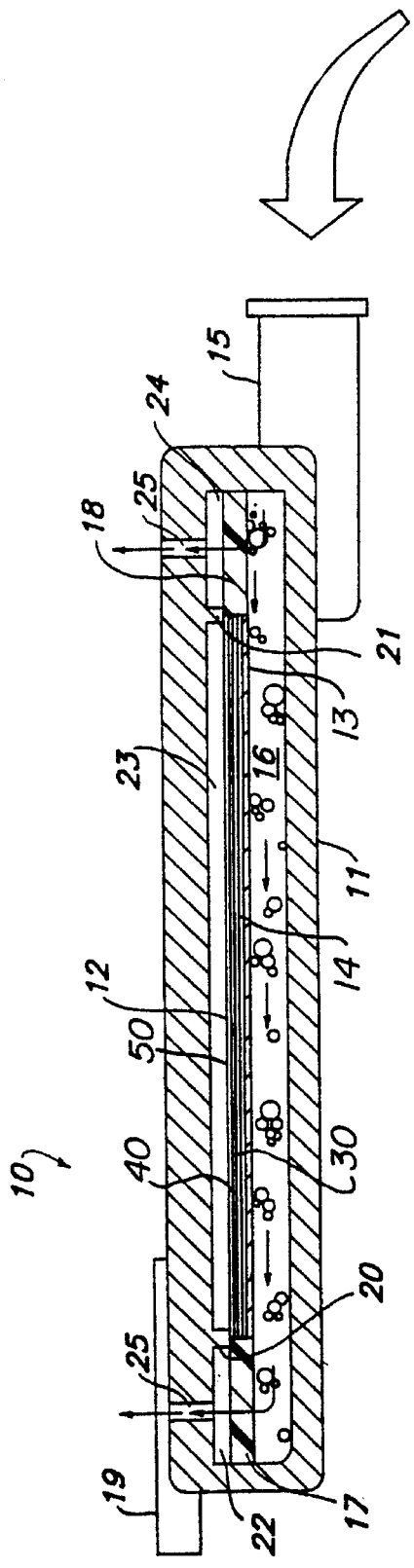
FIG. 5
FIG. 6

METHOD FOR TREATING A PARENTERAL EMULSION-CONTAINING MEDICAMENT FLUID

This application is a continuation-in-part of U.S. Ser. No. 07/620,775, filed Dec. 3, 1990, now U.S. Pat. No. 5,252,222.

TECHNICAL FIELD

This invention relates to a method, system, and device for treating parenteral fluids.

BACKGROUND OF THE INVENTION

The use of parenteral fluids (e.g., involving an administrative pathway other than one which involves the gastrointestinal tract) in health care has grown rapidly over the past several years. For example, since some individuals are unable to receive medication by enteral means, and some medications are less efficient when taken enterally, the use of parenterally administered drugs is preferred.

Parenteral administration typically includes intravascular, intramuscular, or subcutaneous routes, but drugs may be applied to the skin or injected intradermally, for local effect or to be absorbed percutaneously; they may be inhaled for direct action on the bronchial tree or to be absorbed into blood at the alveoli; they may be injected into or near the spinal canal; or they may be introduced intravaginally. Different routes may be used for different reasons. For example, intravascular administration routes may be used to administer large quantities of fluid over a long period of time by means of a continuous infusion apparatus. Also, intravascular administration is usually the safest way to administer a drug that has a narrow margin of safety between therapeutic and toxic blood levels or is easily contaminated. Large amounts of solution may also be introduced intramuscularly, and there is usually less pain and local irritation than is encountered by the subcutaneous route. However, subcutaneous administration may also be advantageous, e.g., when the drug is intended to have local, rather than systematic, effect. With respect to inhalation of drugs, some drugs, particularly volatile anesthetics, may function best when inhaled as aerosols.

Unfortunately, while the parenteral administration of fluids such as medicaments may be advantageous, it is not without drawbacks. For example, infection during the administration process is a potentially major complication, even though medicaments may be produced according to strict regulations, e.g., strict aseptic protocols, and the preparation may be highly uniform. Microbiologic contamination of parenterally administered substances may occur during their preparation, during administration, or via manipulation of a part of the administration set, e.g., a catheter, thus leading to infection. The threat of infection is of particular concern when administering parenteral fluids to debilitated patients with compromised immune systems, since their resistance to infection may be low.

The problem may be magnified since parenterally administered medicaments, particularly those containing lipids, may provide a medium for the rapid growth of potentially pathogenic microorganisms, including bacteria and fungi. For example, fungal organisms, such as *Candida albicans,* and bacterial organisms such as *Escherichia coli, Pseudomonas aeruginosa,* and *Staphylococcus* spp. may thrive in a variety of medicament administration systems, therefore posing a threat of infection.

Additionally, pyrogenic substances, for example, pyrogens of bacterial origin, e.g., endotoxins such as lipopolysaccharide complexes in the parenteral fluid, can induce fever. Moreover, failure to maintain aseptic protocols may lead to infection caused by pathogenic contaminants.

There are additional drawbacks associated with parenterally administered fluids. Part of the problem relates to the composition and characteristics of the parenteral fluid. A typical parenterally administered medicament may include an oil-in-water emulsion wherein lipids are a primary component of the emulsion. The lipid emulsion is typically stabilized by an emulsifying agent such as a phospholipid, which gives the emulsion droplets a negative surface charge, e.g., a zeta potential of about −40 mV. The negatively charged emulsion droplets repel each other, which contributes to the stability of the system by maintaining the homogenous dispersion of the lipid particles within the internal phase of the emulsion. If homogenous dispersion is not maintained, the emulsion may destabilize, and the particles may aggregate in larger numbers, and coalesce to form larger particles. This may pose a great threat to the patient if this parenteral fluid is administered, since particles greater than about 5 micrometers in size may block small pulmonary vessels, causing a potentially dangerous fat embolus.

Additionally, parenterally administered fluids, particularly those containing a lipid emulsion component, may be opaque, making proper inspection for undesirable matter, e.g., large coalesced particles resulting from the instability of the lipid emulsion, particulates, drug-drug coprecipitates, microorganisms, and/or air, impossible. More importantly, visual inspection for undesirable particulate matter is of limited value, since the destabilization of the emulsion would not be visually apparent until the coalesced lipid particles are about 40 to 50 micrometers in size, which is far greater than the minimum size particle (i.e., about 5 micrometers) that might pose a threat to a patient.

Attempts to minimize microbiological contamination and growth in parenteral administration systems have focused on the use of strict aseptic techniques and single-use products, rather than on the use of microbiological filters. For example, microbiological filters are specifically contra-indicated by some manufacturers of parenteral medicaments. It is believed that the filter may cause a breakdown of the emulsion, and the filter may exhibit limited flow capacity, may plug easily and/or may bind or restrict the flow of the medicament. Moreover, the pore rating of a microbiological filter may be expected to block desirable material, such as lipid particles in an emulsion, since those particles may have a diameter of about 0.5 micrometers or less.

All of these situations may present great risk to the patient. If the emulsion breaks down, or the medicament is blocked, the filter and administrative process may be rendered ineffective. If the flow rate is adversely affected, the medical personnel may need to constantly monitor the flow with the fear that the filter may plug and have to be replaced during a medical procedure, which exposes the patient to additional risks, e.g., insufficient medication and/or septic contamination.

Furthermore, the decrease in flow of parenterally administered medicaments which pass through a microbiological filter may pose an additional drawback—excessive pressure build up. Excessive pressure build up may be a serious problem with parenteral systems since the liquid medicament may be administered using a pump designed to operate at relatively low pressures, e.g., less than 25 psi, typically less than 15 psi, and, in some applications, at less than 10 psi. Because these pumps are not engineered to operate at higher pressures, the parenteral fluid administration system typically includes an occlusion alarm which shuts down the pump at a relatively low pressure. This places an additional constraint on the use of anti-microbiological filters having a pore rating below about 1.2 micrometers, since these filters may exhibit pressure build up, flow restriction, and plugging that leads to pump shut down.

Thus, the administration of parenteral fluids, particularly parenteral medicaments, typically reflects an unsatisfying compromise. On the one hand, strict aseptic techniques and single use products may decrease contamination and growth without adversely affecting the emulsion or the flow rate, but these techniques still fail to provide for the administration of a bacteria-depleted infusate to the patient. On the other hand, pore ratings sufficient to remove microorganisms are typically too small to be used effectively with parenteral fluids and with some medicaments administered parenterally. This is an especially unsatisfying compromise since bacteria and/or fungi are likely to grow in media used for parenteral medicaments, especially those medicaments containing a lipid component.

There is, therefore, a need for a filter device for a parenterally administered medicament having an enhanced capability for filtration of undesirable matter from a parenteral medicament fluid, especially to preclude microorganisms and fine particles from entering the infusate while passing the larger, desirable, parenteral medicament fluid components therethrough. In particular, there is an urgent need for a filter for processing a parenteral medicament fluid including a lipid emulsion and a medicament to remove bacteria from an infusate.

SUMMARY OF THE INVENTION

The present invention relates to processes and systems for treating a parenteral medicament fluid to separate undesirable material from the parenteral medicament fluid, and processing the desirable material. For example, parenteral medicament fluids, including those having lipid-based constituents, emulsions, and/or drugs, may be processed to remove biological and/or particulate contaminants from the desirable components of the parenteral medicament fluid.

The processes and systems of the present invention also provide for removal of gas from the assembly and the parenteral medicament fluid.

BRIEF DESCRIPTION OF THE DRAWINGS

FIG. 5 is a longitudinal sectional view taken along the line III—III of the device of FIG. 1.

FIG. 6 is a cross-sectional view taken along the line IV—IV of the device of FIG. 1.

SPECIFIC DESCRIPTION OF THE INVENTION

Figure 1:
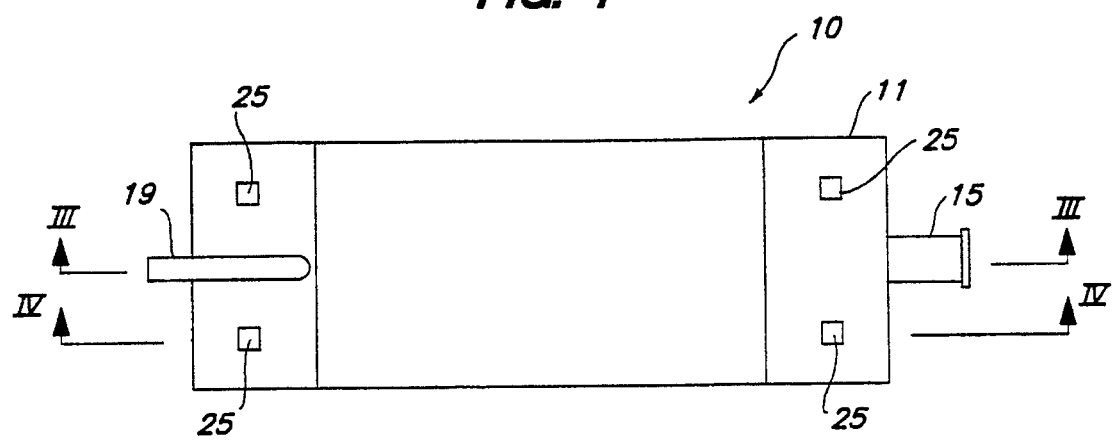
FIG. 1 is a bottom plan view of a parenteral medicament fluid processing device according to the invention.

The present invention provides a method for treating a parenteral emulsion-containing medicament fluid comprising passing a parenteral emulsion-containing medicament fluid to a fluid filtration element, blocking microorganisms and other undesirable material, and passing the parenteral emulsion-containing medicament fluid therethrough.

The present invention also provides a device for treating a parenteral emulsion-containing medicament fluid comprising a fluid filtration element having a microorganism blocking pore rating wherein the fluid filtration element permits the parenteral emulsion-containing medicament fluid to pass therethrough, but blocks microorganisms and other undesirable material.

The present invention also involves a system for treating and administering a parenteral emulsion-containing medicament fluid comprising a parenteral emulsion-containing medicament fluid container in fluid communication with a filter assembly including a fluid filtration element which permits the parenteral emulsion-containing medicament fluid to pass therethrough, but blocks microorganisms and other undesirable material.

The present invention may also provide processes and systems for separating gas from the parenteral emulsion-containing medicament fluid and/or from the filter assembly or system.

As used herein, a parenteral medicament fluid refers to a liquid-based solution or suspension having a medicament, preferably a drug, suitable for administration by means of a non-oral route. Medicament, as used herein, refers to a medicinal agent or any substance used in a therapeutic regimen. In a preferred embodiment, the medicament is a drug or the like. The medicament may be soluble in water, but is preferably non-soluble in water. Non-soluble medicament fluids typically include emulsions, preferably oil-in-water emulsions, and may include amphilic molecules such as lipids. The parenteral medicament fluid may include an emulsion, a solution or a suspension including lipid substances, which are soluble in organic solvents, but are non-soluble, or slightly soluble, in water. Exemplary lipids include fatty acids, such as palmitic acid and linoleic acid; triglycerols (also known as neutral fats), such as tristearin; glycerophospholipids, such as phosphatidic acid or lecithin; sphingolipids, such as gangliosides; and steroids, such as cholesterol. It is intended that the present invention is not to be limited by the number, amount, or type of these substances. The medicament fluids of the present invention may also include any of a number of other substances, including, but not limited to, emulsifying agents, such as phospholipids and the like; stabilizers; vasoconstrictive agents; nutrients, amino acids, electrolytes, trace elements, and vitamins. It is intended that the present invention is not to be limited by the number, amount, or type of these other substances.

The parenteral medicament fluid may also include a number of undesirable materials. The undesirable elements may be present in the fluid as a result of the storage condition or environment, normal metabolic processes, or due to the processing environment, or other causes. As used herein, undesirable material refers to microorganisms, e.g., bacteria and/or fungi, as well as particulate, chemical, and other biological substances which are preferably removed or depleted from the parenteral medicament fluid. Exemplary undesirable materials include but are not limited to particulates, and the like, typically, but not limited to coalesced particles, precipitates, pyrogenic matter such as bacterial endotoxins, administration set contaminants such as ampule and vial material, e.g., glass shards, septa bits, and the like. It is intended that the present invention is not to be limited by the type of undesirable material removed.

Figure 2:
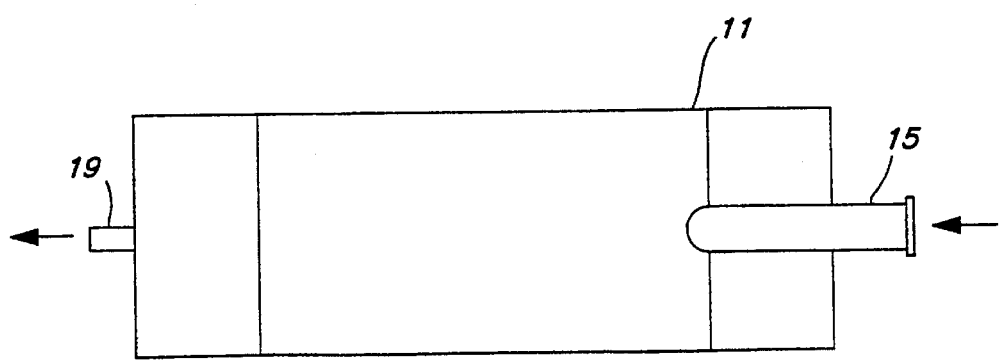
FIG. 2 is a top plan view of the device of FIG. 1.

As illustrated in FIGS. 1 and 2, a parenteral emulsion-containing medicament fluid processing apparatus 10 according to the invention generally comprises a housing 11, preferably transparent, having an inlet 15 and an outlet 19, and defining a fluid flow path between the inlet and the outlet.

As depicted in FIGS. 1–6, in a preferred device 10, the housing 11 may include an inlet 15 and an outlet 19 defining a fluid flow path between the inlet 15 and the outlet 19 with the fluid filtration element 12 disposed across the fluid flow path. The inlet 15 may communicate with a first chamber 16 which is in fluid communication with the fluid filtration element 12 as well as with at least one, more preferably, at least two gas venting elements 17 and 18 for removing gas and the like from the parenteral emulsion-containing medicament fluid and the housing 11. In addition to the chamber 16 depicted in FIGS. 3–6, the housing 11 may have interior walls 20 and 21 which, in combination with the exterior walls for the housing 11, the gas venting elements 17 and 18, and the fluid filtration element 12, may define three additional chambers 22, 23, and 24. Chambers 22 and 24 may include gas vents or outlets 25 for venting to the atmosphere gas separated from and/or displaced by, the incoming fluid.

As illustrated in FIGS. 3–6, the fluid filtration element 12 typically comprises a porous medium which permits an emulsion and a medicament to pass therethrough, but blocks microorganisms and other undesirable material.

Figure 3:
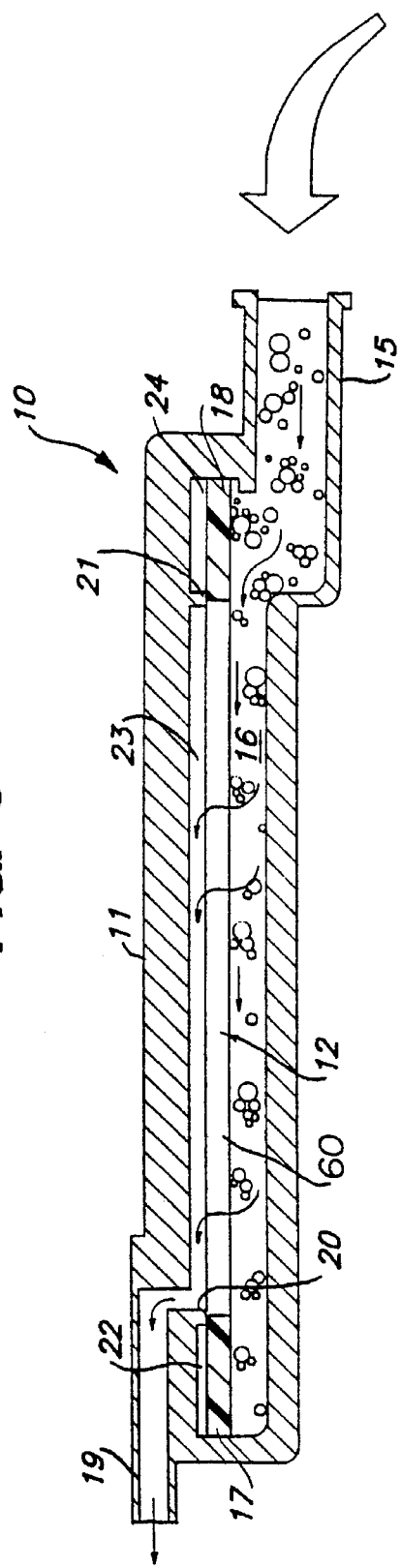
FIG. 3 is a longitudinal sectional view taken along the line III—III of the device of FIG. 1.
Figure 4:
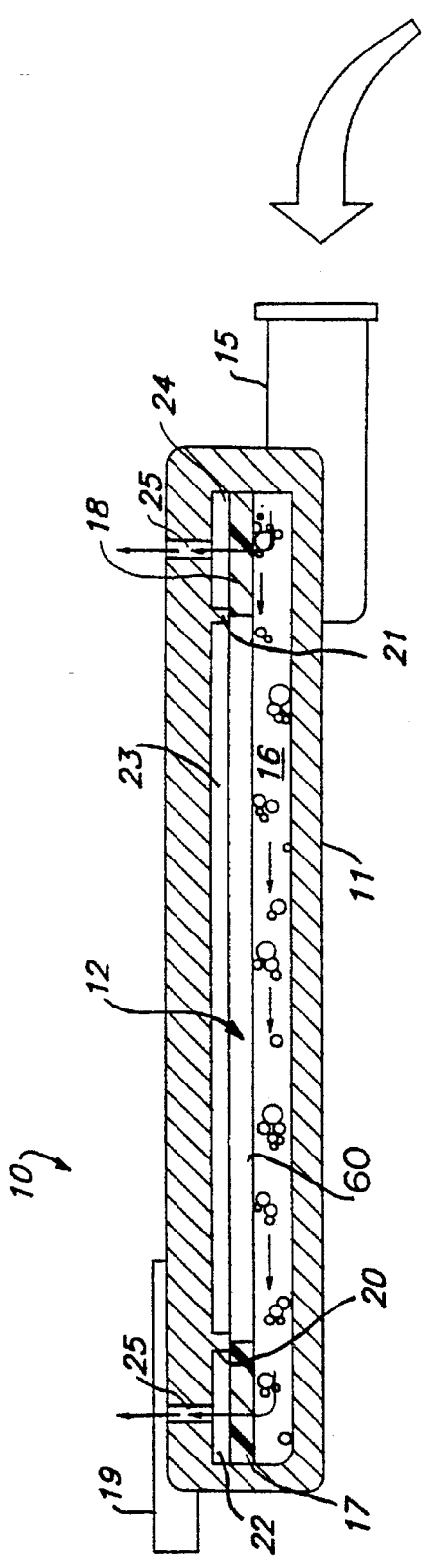
FIG. 4 is a cross-sectional view taken along the line IV—IV of the device of FIG. 1.

In an exemplary embodiment of the invention illustrated in FIGS. 3 and 4, the fluid filtration element 12 may comprise a porous medium having a single layer 60.

In an exemplary embodiment of the invention illustrated in FIGS. 5 and 6, the fluid filtration element 12 may comprise a porous medium having multiple layers, 13, 14, 30, 40, and 50.

The parenteral emulsion-containing medicament fluid processing apparatus 10 may also include at least one, and more preferably, at least two gas venting elements 17 and 18 positioned within the housing 11, to permit gas and the like to pass therethrough, but not parenteral emulsion-containing medicament fluid. Gas in the housing passes through venting elements 17 or 18 through at least one gas vent or outlet 25 for removing gas from the housing 11. In the embodiment of the invention illustrated in FIG. 1, the apparatus includes four vents 25.

Figure 7:
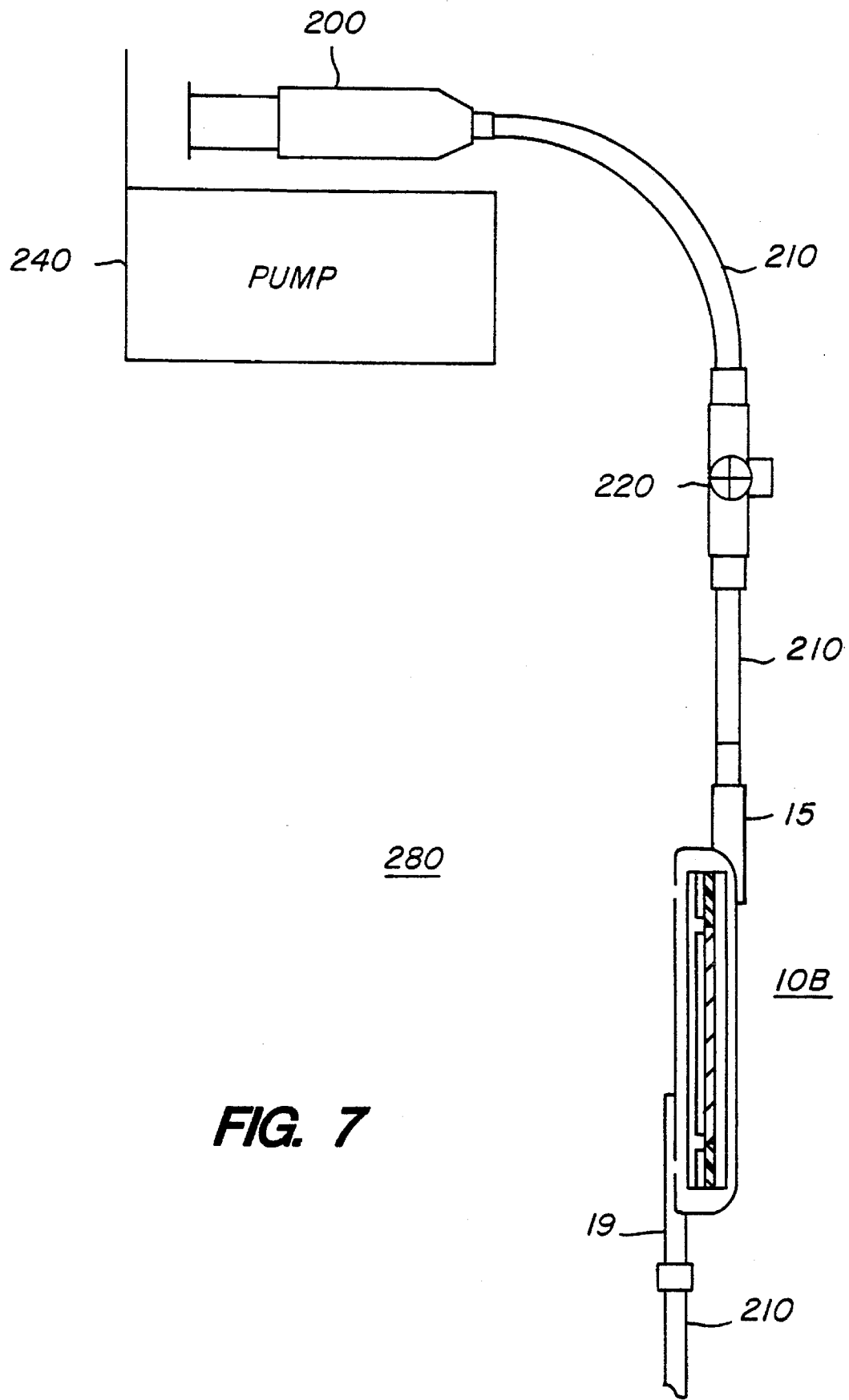
FIG. 7 is an embodiment of a parenteral medicament fluid processing system according to the invention.

A parenteral emulsion-containing medicament fluid administration system according to the invention, as shown in FIG. 7, generally comprises at least one container in fluid communication with a parenteral emulsion-containing medicament fluid processing assembly which includes a fluid filtration element according to the invention.

FIG. 7 shows an exemplary administration system including a parenteral emulsion-containing medicament fluid processing apparatus. Administration set 280 may include at least one container such as syringe 200, and fluid processing apparatus 10B. In a preferred embodiment, container 200 is in fluid communication with parenteral emulsion-containing medicament fluid processing assembly 10B through conduit 210. The illustrated embodiment shows clamp 220 for controlling and/or directing the flow of parenteral emulsion-containing medicament fluid through the system, but other means for controlling and/or directing the flow may be used.

The administration system may also include at least one flow control device, e.g., pump 240, and additional clamps.

Each of the components of the invention will now be described in more detail below.

THE FLUID FILTRATION ELEMENT

The fluid filtration element 12, in accordance with the present invention, comprises at least one porous medium suitable for passing a parenteral emulsion-containing medicament fluid therethrough, without passing microorganisms and other undesirable material. For example, the fluid filtration element may allow desirable components, such as lipids, which are typically about 0.5 micrometers or less in average diameter, and medicaments, to pass through, while blocking material such as coalesced particles and some microorganisms. The fluid filtration medium may also remove smaller material such as other microorganisms (e.g., bacteria), pyrogenic matter, and/or fine particles.

The porous medium, which is preferably microporous, may have a substantially uniform pore size or may include a pore size that varies in a continuous, discontinuous, or stepwise manner. Having varied pore size may contribute to lowering the differential pressure, and may permit passing an increased volume of parenteral emulsion-containing medicament fluid. In a preferred embodiment, the porous medium has a pore size sufficient to block microorganisms and other undesirable substances, e.g., less than about 1.2 micrometers, preferably, less than about 0.8 micrometers, more preferably, less than about 0.5 micrometers, even more preferably, in the range of from about 0.2 to about 0.45 micrometers.

The fluid filtration element may have a single pore rating. In a preferred embodiment, the fluid filtration element includes a pore rating sufficient to block microorganisms and other undesirable substances, e.g., less than about 1.2 micrometers, preferably, less than about 0.8 micrometers, more preferably, less than about 0.5 micrometers, even more preferably, in the range of from about 0.2 to about 0.45 micrometers.

Pore rating, as that term is used herein, refers to the removal rating of a filtration element or porous medium in terms of measuring its efficiency in removing uniform and/or known substances, e.g., uniform diameter polystyrene microspheres in a liquid medium. For example, the pore rating may be determined using a Latex Sphere Test. Typically, a dilute suspension of spheres (0.01 to 0.1 weight percent) is prepared in water containing 0.1 weight percent Triton X-100, an octyl phenoxypolyethoxyethanol with about nine and one-half ethylene oxide units per molecule, available from Rohm & Haas Company. The size of the spheres typically varies from about 0.038 to about 5 microns. They are commercially available from Dow Chemical Company. A volume of about 10 cubic centimeters of the suspension per square inch (of the filtration medium) is passed through the medium and the filtrate is collected in a test tube. The concentration of microspheres in the filtrate can be measured by any number of means, for example, visually, or by use of a nephelometry device (i.e., turbidity meter). The smallest diameter microsphere which is retained at a 99.9% efficiency, i.e., 999 out of 1,000, determines the pore rating.

The fluid filtration element may comprise a porous medium including a single layer. For example, in one embodiment, as illustrated in FIGS. 3 and 4, layer 60 may include a microorganism blocking pore rating, typically about 1.2 to about 0.1 micrometers.

A fluid filtration element according to the invention may also include a porous medium having multiple layers, i.e., two or more layers, and/or may include multiple porous media. The different layers and/or media may include different pore sizes or ratings.

Although a single pore size or pore rating and/or layer may be sufficient for filtering a variety of parenteral emulsion-containing medicament fluids including a lipid emulsion, in those embodiments wherein extensive and/or finer filtration may be desirable, the fluid filtration element may include different pore sizes and/or layers, or the porous media within the fluid filtration element may have different pore sizes, ratings and/or layers, to enhance the filtration. While the mechanism is not well understood, it is believed the filtration may reflect non-permanent deformation of the emulsion as it passes through the fluid filtration element, allowing it to pass through pores that are smaller then the emulsion's normal diameter. Once the emulsion passes through the small pore, it may regain its normal shape and diameter without loss of its desirable characteristics. Different pore sizes and/or pore ratings may enhance filtration, e.g., by progressively deforming the components of the emulsion as they pass through the element, and/or by preventing all of the components of the emulsion from passing through a given pore at the same time, which could restrict flow.

For example, the fluid filtration element may comprise at least two layers, wherein the upstream layer has a coarser rating than the downstream layer, wherein at least the downstream pore rating blocks microorganisms and other undesirable material. The fluid filtration element may also have an intermediate layer with a coarser pore rating than the upstream layer pore rating.

Preferably, in those embodiments comprising at least two layers, the layers have different pore sizes and/or ratings, although the overall pore rating ranges for individual layers may overlap. For example, in one embodiment, as illustrated in FIGS. 5 and 6, the fluid filtration element 12 may comprise a first most upstream layer 13 which may include a pore rating from about 5 to about 1 micrometers, which may be a coarser pore rating than the fifth, most downstream layer 50, which may include a finer, microorganism blocking pore rating of about 1.2 to about 0.1 micrometers. Intermediate layer 40 may include a pore rating of about 50 to about 1 micrometers, and have a coarser pore rating than the most upstream first layer 13. Other inner layers, here shown as second layer 14 and third layer 30, may have finer pore ratings than first layer 13. For example, second layer 14 may include a pore rating from about 3 to about 0.45 micrometers, and third layer 30 may include a pore rating from about 1.2 to about 0.2 micrometers. The selection of pore sizes, ratings and/or layers may be based on achieving a desired result, e.g., a low pressure drop.

While the fluid filtration element may be produced from any suitable material compatible with a parenteral emulsion-containing medicament fluid, practical considerations dictate that consideration be given first to the use of commercially available materials. The liquid filtration element of this invention may be preferably formed, for example, from any natural or synthetic material capable of forming fibers or a membrane. Suitable polymers include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene difluoride (PVDF), polyethylene, polypropylene, polybutylene terephthalate (PBT), polyethylene terephthalate (PET), and any nylon, e.g., Nylon 6, 11, 46, 66, and 610. Preferred polymers are polyolefins, polyesters, and polyamides. Especially preferred are nylon and PBT.

Other suitable materials include cellulosic derivatives, such as cellulose acetate, cellulose propionate, cellulose acetate-propionate, cellulose acetate-butyrate, and cellulose butyrate. Non-resinous materials, such as glass fibers, may also be used.

Exemplary membranes are disclosed in U.S. Pat. No. 4,906,374. Other membranes, including those disclosed in U.S. Pat. Nos. 4,886,836; 4,964,989; 5,019,260; 4,340,479; 4,855,163; 4,774,132; 4,702,840; 4,707,266; 4,203,848 and 4,618,533, may also be suitable.

Particularly preferred are commercially available media, such as those available from Pall Corporation under the trademarks LOPRODYNE® (membranes) and HDC® (fibrous media). Commercially available membranes, such as those available from Pall Corporation under the trademarks ULTIPOR N66®, ULTIPOR®, FLUORODYNE®, POSIDYNE®, CARBOXYDYNE®, IMMUNODYNE®, BIODYNE A®, BIODYNE B®, and BIODYNE C®, may also be suitable.

The membrane may comprise a microporous membrane, more preferably a skinless microporous membrane. A microporous membrane, as the term is used herein, refers to a thin sheet, generally formed from a synthetic plastic material, having a substantially uniform, continuous matrix structure containing myriad pores typically ranging from a few micrometers to about 0.04 micrometers in diameter.

The fibrous medium may comprise a fibrous matrix, more preferably, a microfibrous matrix. A microfibrous matrix, as the term is used herein, indicates a sheet-like web, or a three-dimensional network of fibers, whether melt-blown, staple, or continuous, which together form a coherent structure suitable for use as a filter medium. Preferred microfibrous matrices are made from melt-blown thermoplastic polymeric fibers, where the fiber diameter is typically in the range of from about 0.5 to about 20 micrometers, more preferably in the range of from about 1 to about 4 micrometers.

In one embodiment of the invention, the fibrous medium comprises a synthetic, polymeric microfibrous matrix. A microfibrous matrix, partially as a result of its dirt capacity, may be more resistant to pressure build up and clogging. Additionally, a microfibrous matrix may be preferred because of its enhanced dirt capacity when compared to a microporous membrane. Moreover, a microfibrous matrix may enhance the deformation of the desirable component, e.g., a lipid particle, as the component passes through the microfibrous matrix. This deformation may be desirable in enhancing the material's ability to pass through a fine pore. Finally, the microfibrous matrix may enhance filtration by acting as a spacer. For example, in those embodiments including a membrane layer downstream of the microfibrous matrix layer, the spacer effect may prevent all of the particles from contacting the upstream surface of the membrane at the same time, which could restrict flow through the membrane.

The fluid filtration element may remain untreated, or the fibers or membrane may be treated to increase its effectiveness. There are a number of methods for treating the fluid filtration element to increase its effectiveness. For example, the fibers and/or the membrane may be surface modified to provide a low affinity for amide or peptide group-containing materials, particularly proteinaceous materials. The fibers and/or the membrane may be surface modified to affect the critical wetting surface tension (CWST) of the element. The fibers and/or membrane may be modified with a charge modifying agent to produce a negatively or positively charged medium, and/or a negative or positive zeta potential. Preferably, the fibers and/or the membrane are charge neutral.

Surface characteristics of a fiber and/or membrane can be modified by chemical reaction including wet or dry oxidation, by coating or depositing a polymer on the surface, or by a grafting reaction. Grafting reactions may be activated by exposure to an energy source such as gas plasma, heat, a Van der Graff generator, ultraviolet light, or to various other forms of radiation, or by surface etching or deposition using a gas plasma treatment. The preferred method for a grafting reaction uses gamma-radiation, for example, from a cobalt source. The preferred method for gas plasma treatment uses a low temperature gas plasma. More preferably, the gas plasma is an inorganic gas, for example, oxygen.

An exemplary technique for gas plasma treatment may employ at least one of an inorganic and organic gas, which may be a vaporized organic material such as an ethylenic monomer to be plasma polymerized or deposited on the surface of the substrate (e.g., the fibers and/or membrane). A typical technique, e.g., radio frequency (RF) discharge, involves placing a substrate to be gas plasma treated in a vacuum chamber and bleeding gas at low pressure into the system until the desired gas pressure differential is obtained. An electromagnetic field may be generated by subjecting the gas to a capacitive or inductive RF electrical discharge. The gas absorbs energy from the electromagnetic field and ionizes, producing high energy particles. The resultant plasma modifies the fibers or medium in the plasma zone.

Inorganic gases suitable for use in gas plasma treatment may be exemplified by helium, argon, nitrogen, neon, nitrous oxide, nitrogen dioxide, oxygen, air, ammonia, carbon monoxide, carbon dioxide, hydrogen, chlorine, hydrogen chloride, bromine cyanide, sulfur dioxide, hydrogen sulfide, xenon, krypton, and the like. Suitable organic gases may be exemplified by acetylene, pyridine, gases of organosilane compounds and organopolysiloxane compounds, fluorocarbon compounds and the like.

As noted earlier, the fibers and/or membrane may be treated to modify the CWST of the fluid filtration element. For example, the fibers and/or membrane may be subjected to radiation or a plasma stream in the presence of an acrylic monomer such as hydroxethyl methacrylate (HEMA) or hydroxypropyl acrylate (HPA) to increase the CWST of the element. Preferably, the fluid filtration element according to the invention includes a CWST in the range of about 30 dynes/cm to about 115 dynes/cm. In one embodiment, the fluid filtration element is hydrophilic, i.e., having a CWST greater than 72 dynes/cm. In a more preferred embodiment, the CWST may be in the range from about 75 to about 90 dynes/cm.

As used herein, and as disclosed in U.S. Pat. No. 4,954, 256 and in greater detail in U.S. Pat. No. 4,925,572, the CWST of a porous medium, in units of dynes/cm, is defined as the mean value of the surface tension of the liquid which is absorbed and that of the liquid of neighboring surface tension which is not absorbed within a predetermined amount of time. The absorbed and non-absorbed values depend principally on the surface characteristics of the material from which the porous medium is made and secondarily on the pore size characteristics of the porous medium.

In a preferred embodiment, the fluid filtration element may be surface modified by grafting thereon a hydroxyl-containing monomer to provide an element having a low affinity for amide or peptide-group containing materials, e.g., proteinaceous materials. As used herein, low affinity for proteinaceous materials refers to adsorption of less than about 100 micrograms per square centimeter of proteinaceous materials as measured by the Bovine Serum Albumin Adsorption test. In a more preferred embodiment, the adsorption of proteinaceous material is less than about 35 micrograms per square centimeter.

For example, as described in U.S. Pat. No. 4,906,374, the fluid filtration element of this embodiment of the invention may be a polymeric substrate which may be surface modified using hydroxyl-containing unsaturated monomers, more typically monofunctional unsaturated monomers rich in pendant hydroxyl groups or groups capable of reacting to form hydroxyl groups, which are capable of undergoing polymerization and covalently bonding to the substrate under the influence of ionizing radiation.

Preferred monomers have moieties characterized by ethylenic or vinylic unsaturation and hydroxyl groups. Preferred monomers include hydroxyalkyl acrylates in which the "alcoholic" or hydroxyl-containing portion of the molecule (as opposed to the portion of the molecule "derived" from a carboxylic acid) constitutes a substituted lower alkyl group having from 2 to 5 carbon atoms, preferably from 2 to 3 carbon atoms. The substituent is preferably a hydroxyl group. Mixtures of monomers may also be used. The most preferred hydroxyl-containing monomers are those in which the hydroxyl group is pendant, i.e., the group is not attached to a carbon atom which forms part of the polymer's backbone but is bound to a carbon atom that is separated from the backbone as, for example, a branching carbon atom. Exemplary preferred monomers include 2-hydroxyethyl acrylate, 2-hydroxyethyl methacrylate, 3-hydroxypropyl acrylate, and 3-hydroxypropyl methacrylate, which may be commercially available from, for example, Rohm and Haas Chemical Company under the trademark ROCRYL®.

In addition to the structural features designated above, suitable monomers may also be further characterized by their properties, such as responding to ionizing radiation by forming a free radical. Suitable monomeric compounds should be substantially completely, if not totally, soluble in the solvents used. Preferred solvents include polar solvents, particularly hydroxylated solvents such as water, lower aliphatic alcohols, such as ethanol, and mixtures thereof.

Solutions of the monomer compound may range in concentration of the monomer(s) from about 0.1 to about 5.0 percent, by weight, preferably about 0.2 to about 3.0 percent, by weight, based on the total weight of the solution. The procedure used to saturate the porous polymeric support is known to one of skill in the art. For example, batch or continuous processes may be suitable. After saturation, the monomer(s) may be polymerized and covalently bound to the polymeric substrate under the influence of ionizing radiation, more preferably, gamma radiation or short wavelength ultraviolet radiation.

The fluid filtration element may be fashioned in a variety of ways. For example, it may include one or more of the following: a web, a sheet, and a depth filter. The fluid filtration element may be formed into any geometric shape or form suitable for passing a parenteral emulsion-containing medicament fluid therethrough. Preferably, the fluid filtration element comprises at least one flat planar sheet, although in a less desirable embodiment, it may comprise at least one sheet formed into a pleated, corrugated, or accordion form.

The fluid filtration element, which may be fibrous and/or membranous, may comprise a composite or a multilayer arrangement. Layers may be individually prepared and bonded together by various means known to those skilled in the art. For example, the fluid filtration element may include compressed and/or co-dried layers. Layers may be contiguous and/or separate. The fluid filtration element may be preformed to form an integral unitary structure. The fluid filtration element may also include additional constituents, including, but not limited to at least one layer to provide support and/or better drainage. Exemplary supports and/or drainage components are non-woven polyester or polypropylene mesh.

The layers or porous media which constitute the fluid filtration element may be arranged in a variety of ways with respect to fluid flow. For example, a fibrous medium may be interposed between at least one upstream membrane and at least one downstream membrane. In one embodiment, the fluid filtration element may comprise three upstream membrane layers, followed by the fibrous layer and the downstream membrane. The membrane layers may have decreasing pore ratings in the upstream to downstream direction. The fibrous layer may have a coarser pore rating than at least one of the upstream membrane layers.

The fluid filtration element of devices made in accordance with this invention may be preformed to controlled dimension and pore size and/or rating in order to form an integral, self-contained element prior to assembly in a housing. Preforming eliminates the pressure on the inlet and outlet faces of the container which may be inherent, e.g., in a packed fiber system. Pre-forming the element typically leads to devices having longer service life, coupled with better removal of undesirable material and less hold up of fluid, when compared to devices that use fibers or fibrous webs packed in a housing at assembly.

A fluid filtration element produced in accordance with the present invention for passing parenteral emulsion-containing medicament fluid preferably may have a flow area of about 0.65 cm$^2$ to about 929 cm$^2$ (about 0.1 to about 144 in$^2$), more preferably in the range from 0.65 cm$^2$ to about 97 cm$^2$ (about 0.1 to about 15 in$^2$). As used herein, the term flow area refers to the face surface area contacted by the parenteral emulsion-containing medicament fluid.

A preferred relative voids volume may be in the range of about 50% to about 90%, more preferably in the range of from about 60% to about 85%. The thickness of the fluid filtration element may be in the range of from about 0.008 cm to about 0.25 cm (about 0.003 inches to about 0.100 inches), more preferably in the range of from about 0.013 cm to about 0.25 cm (about 0.005 to about 0.100 inches). The fiber surface area of the fluid filtration element may be in the range of from about 0.2 to about 2.5 M$^2$/g, preferably from about 0.5 to about 2 M$^2$/g.

In other embodiments that may involve lower flow rates and/or volumes of parenteral emulsion-containing medicament fluids, e.g., involving parenteral emulsion-containing medicament fluids for neonatals, the element area may be adjusted as necessary.

Included within the scope of the present invention are the use of other pore ratings, pore sizes and/or arrangements of fibers and membranes, with respect to particular layers as well as throughout the fluid filtration element. These alternatives may be chosen based on achieving a desired result, e.g., relating to the flow rate, the pressure drop, the type of fiber and/or membrane used, as well as other considerations.

GAS VENTING ELEMENT

A filter device of the subject invention may include at least one, and more preferably, two, gas venting elements 17 and 18, each comprising at least one porous medium which is liquid-repellant or non-wettable by the parenteral emulsion-containing medicament fluid and which allows gas that may be present in the parenteral emulsion-containing medicament fluid and the assembly to pass out of the device, for example, through vent 25. In a preferred embodiment, the gas venting element comprises at least one microporous membrane.

The gas venting element may vent gas from the system, in order to prime the device and eliminate any extraneous gas. This may be desirable since the presence of gas may reduce the efficiency of the fluid filtration element, e.g., by blocking the filtration element. Preferably, the gas venting element may prevent gas from being administered, e.g., to a patient.

As used herein, gas refers to any gaseous fluid, such as air, sterilized air, oxygen, carbon dioxide, and the like; it is intended that the invention is not to be limited thereby.

The gas venting element may be oriented in a variety of ways with respect to the flow of the parenteral emulsion-containing medicament fluid. For example, the gas venting element may be located in any of the various components of the filter assembly or the administration system. By way of illustration, at least one gas venting element may be included in at least one of the conduits used to connect the various components of the administration system, in a wall of a container, or in a port on or in one of the containers or the filter assembly. Generally, however, it is preferred to include the gas venting element within the filter assembly located in the same plane as the fluid filtration element.

The gas venting element should have the necessary strength to handle the pressures encountered in use and have the ability to provide the desired permeability without the application of excessive pressure.

The gas venting element may be produced from any suitable material which is compatible with the parenteral emulsion-containing medicament fluid. While a variety of materials may be used, practical considerations dictate that consideration be given first to the use of commercially available materials. The gas venting element may be formed, for example, from the materials listed above with respect to the liquid separation element. Preferred polymers are polyolefins, polyesters, polyamides, polyurethanes, polysulfones, and fluoropolymers such as polyvinylidene difluoride, polytetrafluoroethylene, and perfluoroalkoxy resins. Particularly preferred are fluoropolymers, more preferably, polytetrafluoroethylene (PTFE).

Exemplary gas venting elements include, but are not limited to, those disclosed in U.S. Pat. No. 4,954,256, and International Publication No. WO 91/17809.

The gas venting element may be untreated, or treated or modified to make it more effective. The element may be liquophobic. A liquophobic gas venting element in the context of this invention is one that has a critical wetting surface tension lower than the surface tension of the parenteral emulsion-containing medicament fluid, or is not readily or spontaneously wetted by the parenteral emulsion-containing medicament fluid. Because the liquophobic element is not wettable, or poorly wettable, by the parenteral emulsion-containing medicament fluid being treated or processed in the system, gas in the system that contacts the liquophobic medium may pass through it, while the parenteral emulsion-containing medicament fluid may not.

The gas venting element may be treated to increase its liquophobicity. For example, the element may be surface modified to decrease the critical wetting surface tension (CWST), with the term CWST being as defined above with respect to the fluid filtration element.

In one embodiment, the gas venting element may have a CWST of less than about 28 dynes/centimeter, rendering it liquid-repelling or non-wetting by liquids with surface tensions well below that of water's surface tension of 72 dynes/centimeter.

Surface characteristics of the gas venting element may be modified by a number of methods, including those described above with respect to the fluid filtration element.

In a preferred embodiment of the gas venting element according to the subject invention, the element may comprise an untreated PTFE microporous membrane commercially available from, for example, W. L. Gore Associates, Inc.

In another embodiment of the gas venting element of the subject invention, the element may be surface modified by bonding thereon one or more fluorine-containing monomers. For example, as described in U.S. Pat. No. 4,954,256, a porous structure, preferably a microporous, polymeric membrane comprising a fluoropolymer substrate, more preferably a poly(vinylidene fluoride) membrane substrate, may be saturated with a solution comprising one or more polymerizable fluorine-containing monomers containing an ethylenically unsaturated group and a fluoroalkyl group in a suitable solvent, and exposed to gamma radiation to form a superstrate fluoropolymer chemically bonded to the membrane.

The selected pore rating of the gas venting element may effectively preclude wetting at the operating pressures utilized for processing the parenteral emulsion-containing medicament fluid. For example, a gas venting element having a pore rating of about 0.02 micrometers operated in a typical administration system may vent gas without passing parenteral emulsion-containing medicament fluid therethrough.

With respect to pore ratings, since the gas venting element may be open to the atmosphere to allow the gas to be vented, which could allow bacteria to enter, the pore rating should be about 0.3 micrometers or less, more preferably in the range of about 0.2 to about 0.02 micrometers, to preclude bacteria from entering either the system or the parenteral emulsion-containing medicament fluid.

The gas venting element may include a plurality (i.e., two or more) of layers. The element may include additional constituents, including, but not limited to, at least one liquophilic layer and/or at least one layer to provide support. As used herein, liquophilic refers to a medium that has a critical wetting surface tension higher than the surface tension of the parenteral emulsion-containing medicament fluid, or is readily or spontaneously wetted by the parenteral emulsion-containing medicament fluid. As with the fluid filtration element, the layers of the gas venting element may be individually prepared and bonded together by various means known to those skilled in the art.

FILTER ASSEMBLY

The fluid filtration element 12, with or without the gas venting element 17 and 18, may be positioned across the parenteral emulsion-containing medicament fluid flow path within a housing 11 having an inlet 15 and an outlet 19 to form a filter assembly. The parenteral medicament fluid filter assembly may comprise any housing containing a fluid filtration element suitable for passing emulsion and medicament therethrough, but blocking microorganisms and other undesirable material.

The housing may be fabricated from any suitably rigid, impervious material, including any impervious thermoplastic material, which is compatible with the fluid being processed. For example, the housing may be fabricated from a metal, such as stainless steel, or from a polymer. In a preferred embodiment, the housing is fabricated by injection molding from a polymer, more preferably a transparent or translucent polymer, such as an acrylic, polypropylene, polystyrene, or a polycarbonated resin. Not only is such a housing easily and economically fabricated, but also it allows observation of the passage of the liquid through the housing. The housing may include an arrangement of one or more channels, grooves, conduits, passages, ribs or the like which may be serpentine, parallel or curved, or a variety of other configurations to provide for more efficient flow of parenteral emulsion-containing medicament fluid and/or gas.

The surfaces of the housing contacting the fluid may be treated or untreated. For example, the surfaces of the housing contacting the fluid may be rendered liquophilic for better priming. Methods for treating the surface of the housing include but are not limited to radiation grafting and gas plasma treatment.

Any housing of suitable shape to provide an inlet, an outlet, and an adequate flow area may be employed. The filter assembly in accordance with this invention may be fashioned in a variety of configurations including, but not limited to, those described in U.S. Pat. No. 3,803,810.

Preferably, the filter assembly may have a hold up volume of about 25 milliliters or less. A preferred configuration, as depicted in FIGS. 1–6, can be constructed with a hold up volume of less than about 5 milliliters, more preferably, less than about 2 milliliters.

All of the components of the filter assembly may be variously configured with respect to parenteral emulsion-containing medicament fluid flow. For example, the inlet 15 may be configured as a spike which can be inserted into a container of parenteral emulsion-containing medicament fluid. Alternatively, as shown in the drawings, both the inlet and the outlet can be configured as tube connectors. The chambers may be configured in a variety of ways, e.g., to maximize fluid contact with the fluid filtration element, minimize hold up volume, and/or decrease the pressure drop.

In a less desirable embodiment, gas venting element may be located in a separate housing or conduit, with or without at least one of the following: a chamber; a gas vent or outlet; a cap; and a clamp.

The fluid filtration element may be sealed or fit within the housing to achieve convenience of use, rapid priming, and efficient air clearance. For example, the fluid filtration element may be compression sealed or interference fit within the housing. Other suitable techniques for sealing or fitting the medium within the housing are included within the scope of the present invention.

The fluid filtration assembly in accordance with the invention may be fashioned to operate at the range of pressures encountered in use. For example, the fluid filtration assembly typically operates at pressures of less than about 25 psi, more preferably less than about 15 psi, and even more preferably, less than about 10 psi.

Since different parenteral emulsion-containing medicament fluids may be administered in different quantities, for different amounts of time and/or at different rates, the volumetric capacity of the assembly may vary. For example, a typical volumetric capacity for a parenteral emulsion-containing medicament fluid such as an anesthetic may be less than about 1 liter, more preferably, in the range of from several milliliters to about 100 milliliters.

ADMINISTRATION SET

The filter assembly may be incorporated into a parenteral emulsion-containing medicament fluid processing and/or administration set.

The containers 200 which may be used in the parenteral emulsion-containing medicament fluid administration set may be constructed of any material compatible with a parenteral emulsion-containing medicament fluid. The composition of the container may vary on the nature of the parenteral emulsion-containing medicament fluid or fluids utilized. A wide variety of suitable containers are already known in the art. Typically, container 200 may be composed of a flexible material, for example, polyvinyl chloride (PVC). Alternatively, the containers may be composed of a non-flexible material, for example, polypropylene, acrylonitrile butadiene styrene (ABS), polycarbonate, or stainless steel. Exemplary containers include a syringe or a flexible bag. It is intended that the invention should not be limited by the type or composition of the container being employed.

As with the containers, the conduits 210 may be constructed of any material that is compatible with the parenteral medicament fluid, preferably PVC. As used herein, the conduits are any tubing or means which provide fluid communication between the various components of the administration set. A clamp, seal, stopcock, valve, transfer leg closure, or the like, may be in fluid communication with at least one of the conduits in order to facilitate a desired function, i.e., establishing a desired flow path for parenteral medicament fluid and/or gas.

It is intended that the present invention is not to be limited by the above listed components of the administration set. For example, the parenteral medicament fluid administration set may have components such as, but not limited to, additional containers, means to provide fluid communication and/or establish a desired flow path, and injection ports.

METHOD

The invention also includes methods for treating and administering a parenteral emulsion-containing medicament fluid comprising passing an emulsion-containing medicament fluid to a fluid filtration element, blocking microorganisms and other undesirable material, and passing desirable components of the parenteral medicament fluid therethrough. A method according to the invention may also include passing gas present in the filter assembly and/or in the parenteral medicament fluid through a gas venting element, and blocking the parenteral medicament fluid from passing therethrough. A method may also include further processing the treated parenteral medicament fluid by administering it to a patient.

Using FIGS. 1–6 for reference, a method according to the invention may include passing a parenteral emulsion-containing medicament fluid into filter assembly 10 via the inlet 15, and, as depicted by the arrows in FIG. 3, into chamber 16. The parenteral medicament fluid then passes through the fluid filtration element 12 into chamber 23, and passes out of the filter device 10 via the outlet 19. Passing the medicament fluid through the fluid filtration element may include blocking microorganisms and other undesirable substances from passing therethrough. Passing gas present in the parenteral medicament fluid and/or the filter assembly may include passing gas into the chamber 16 and, as depicted by the arrows in FIG. 4, passing the gas freely through the gas venting elements 17 and 18 into the chambers 22 and 24 and out the gas outlets or vents 25.

An exemplary method may also include treating a parenteral emulsion-containing medicament fluid by passing it through an administration system wherein the parenteral medicament fluid in a container is passed from the container through a conduit and a filter assembly which includes a fluid filtration element. Passing the parenteral emulsion-containing medicament fluid through the fluid filtration element may include blocking microorganisms and other undesirable material.

For example, as shown in FIG. 7, clamp 220 is opened, and a pressure differential is created, e.g., by depressing the plunger on syringe 200, such that parenteral emulsion-containing medicament fluid passes from the container 200, through conduit 210, and through the filter assembly 10B. As fluid passes through the system, gas ahead of the fluid may be passed out of the filter assembly 10B through vents 17 and 18 and outlets 25. As the parenteral medicament fluid passes through the filter assembly 10B, desirable components of the parenteral emulsion-containing medicament fluid pass through the fluid filtration element within the assembly, while microorganisms and other undesirable material are blocked. The filtered medicament fluid then passes out of the filter assembly 10B, through conduit 210, and into another container or into the patient.

With respect to administration of the treated parenteral emulsion-containing medicament fluid, a flow control device, e.g., a pump 240, more preferably an infusion pump, even more preferably an infusion pump with at least one occlusion alarm (not shown) located either upstream or downstream of the filter assembly may be used to control the flow rate during administration. It is intended that the present invention is not to be limited by the use or type of flow control device.

Flow rates of the fluid may range from about several milliliters per hour to about 2000 milliliters per hour, as desired. A typical flow rate for a parenteral emulsion-containing medicament fluid may be from about 60 milliliters per hour to about 2000 milliliters per hour. In a more preferred embodiment, passing the parenteral emulsion-containing medicament fluid through the fluid filtration element 12 removes microorganisms and other undesirable material from the parenteral emulsion-containing medicament fluid with a pressure drop of about 20 psi or less, preferably about 15 psi or less, and even more preferably, 10 psi or less while passing the parenteral emulsion-containing medicament fluid at a flow rate of up to about 1200 milliliters per hour.

If desired, additional fluids, including parenteral medicament fluids, may be introduced into the system through other components of the administration set, e.g., injection ports and/or connectors located upstream and/or downstream of the filter assembly.

In a less desirable embodiment, gas may be separated from the parenteral emulsion-containing medicament fluid through a gas venting element that does not act in concert with the fluid filtration element. For example, gas venting element may be located downstream, or, more preferably, upstream, of the filter assembly, e.g., in a separate housing located in conduit 210. For example, the venting element may be located upstream of the filter assembly, and a clamp 220 located between the filter assembly and the venting element may be closed, so that creating a pressure differential causes gas displaced by the parenteral emulsion-containing medicament fluid to pass through the venting element. Once the gas has been displaced, the clamp may be opened. The gas venting element may include an additional liquophilic layer that, once wetted, precludes the entrance of air. Preferably, the layers are oriented so that the parenteral emulsion-containing medicament fluid may contact the liquophilic layer before contacting the liquophobic layer. In another embodiment, the configuration of the housing including the gas venting element may provide for capping and uncapping the gas venting element as desired.

EXAMPLES

The filter assemblies used in the following Examples were primed before testing as follows: A 60 cc syringe was filled with a parenteral emulsion-containing medicament fluid. The filter assembly was held above the level of the syringe, and, while holding the assembly with the outlet facing up, the plunger of the syringe was manually depressed, causing the parenteral emulsion-containing medicament fluid to flow through the assembly, while gas flowed through the venting element and exited from the assembly. The housing was tapped gently to dislodge air bubbles. Once primed, the filter assembly was tested as noted below.

The parenteral emulsion-containing medicament fluid used in the following Examples was DIPRIVAN® (Stuart Pharmaceuticals), which is a hypnotic agent for use in the induction and maintenance of anesthesia. DIPRIVAN® includes propofol in an oil-in-water emulsion which also includes soybean oil, glycerol, lecithin and sodium hydroxide. Propofol is chemically described as 2,6-diisopropylphenol, with a molecular weight of 178.27

EXAMPLE 1

A filter assembly having a housing, a fluid filtration element in the form of a flat microporous ULTIPOR $N_{66}$® membrane having a microorganism blocking pore rating as noted below, and a CWST of 76±4 dynes/cm, along with two gas venting elements, which were flat PTFE membranes (W. L. Gore Associates, Inc.), each having a nominal pore rating of about 0.02 micrometers and a CWST of 23 dynes/centimeter, was used in the three tests in this Example.

In the first two tests, the fluid filtration element was a microporous ULTIPOR $N_{66}$® membrane, supported as disclosed in U.S. Pat. No. 4,340,479, with a microorganism blocking pore rating of about 0.45 micrometers.

The fluid filtration element in the third test, which had a microorganism blocking pore rating of 0.2 micrometers, was formed by co-drying two microporous ULTIPOR $N_{66}$® membranes, the upstream membrane having a pore rating of about 0.2 micrometers, and the downstream membrane having a pore rating of about 0.8 micrometers.

The fluid filtration element and gas venting elements were sealed in a housing to form a filter assembly as generally described with respect to FIGS. 1–6.

Tubing was connected from the outlet to a 50 ml graduated cylinder. Tubing was connected from the inlet to a 60 cc plastic syringe, with a 0–15 psi pressure gauge interposed in the tubing between the syringe and the inlet. The syringe had been previously filled with 60 ml of DIPRIVAN®, and the filter assembly had been primed as noted above. The syringe was mounted in a Harvard Apparatus Inc. programmable syringe pump (Model 44).

The Harvard pump was programmed to run at a bolus (or induction) rate of 20.0 ml/min for 20 ml of DIPRIVAN®, and operated according to the manufacturer's instructions. Three tests were performed, and the pressure was recorded during each test, with the following results:

Test 1 (pore rating of about 0.45 micrometers). Final pressure was about 9.2 psi.

Test 2 (pore rating of about 0.45 micrometers). Final pressure was about 9.3 psi.

Test 3 (pore rating of about 0.2 micrometers). Final pressure was about 12.0 psi.

Example 1 showed that fluid filtration elements having membranes with microorganism blocking pore ratings of about 0.45 and about 0.2 micrometers will pass a parenteral emulsion-containing medicament fluid therethrough at a bolus rate of 20.0 ml/min.

EXAMPLE 2

A filter assembly having a fluid filtration element with a microorganism blocking pore rating of about 0.45 micrometers was set up and tested as generally described with respect to FIG. 1, with the exception that the Harvard pump was programmed to run at a maintenance rate of 1.0 ml/min for 20 ml of Diprivan®.

Pressure was recorded several times during the test, with the following results:

| volume (ml) | pressure (psi) |
| --- | --- |
| 3.5 | .5 |
| 5.0 | 1.3 |
| 6 | 1.7 |
| 7 | 2.1 |
| 9 | 2.8 |
| 10 | 3.2 |
| 12 | 3.8 |
| 14 | 4.3 |
| 15 | 4.6 |
| 17 | 5.2 |
| 18 | 5.4 |
| 20 | 5.9 |

Example 2 showed that a fluid filtration element having a membrane with a microorganism blocking pore rating of about 0.45 micrometers will pass a parenteral emulsion-containing medicament fluid therethrough at a maintenance rate of 1.0 ml/min.

EXAMPLE 3

The filter assembly used in this example was set up and tested as in the previous examples, with the following exceptions: 1) the fluid filtration element was a LOPRODYNE® membrane having a microorganism blocking pore rating of about 0.45 micrometers and a CWST of 83 dynes/cm, and an adsorption of proteinaceous material as measured by the Bovine Serum Albumin Adsorption test of less than about 15 micrograms per square centimeter, and 2) the same filter assembly was tested at an induction rate of 20.0 ml/min for 20 ml of DIPRIVAN®, and then at a maintenance rate of 1.0 ml/min for 40 ml of DIPRIVAN®.

The results are listed below. The first value (i.e., at 20.0 ml) reflects the pressure at the induction rate, while the remaining values reflect the pressures at the maintenance rate.

| volume (ml) | pressure (psi) | |
| --- | --- | --- |
| 20.0 | 5.8 | induction rate |
| 20.5 | 1.3 | maintenance rate |
| 21.0 | 2.0 | |
| 23.0 | 2.7 | |

-continued

| volume (ml) | pressure (psi) |
|---|---|
| 25.0 | 3.0 |
| 30 | 3.7 |
| 35 | 4.3 |
| 40 | 4.8 |
| 45 | 5.4 |
| 50 | 5.8 |
| 55 | 6.3 |
| 60 | 6.8 |

Example 3 demonstrated that a fluid filtration element having a membrane which has a microorganism blocking pore rating of about 0.45 micrometers and a low affinity for amide-group containing materials will pass a parenteral emulsion-containing medicament fluid including a lipid emulsion therethrough, with less of a pressure drop than other membranes having similar microorganism blocking pore ratings. Furthermore, Example 3 demonstrated this at different rates, i.e., at a bolus rate of 20.0 ml/min, and at a maintenance rate of 1.0 ml/min.

EXAMPLE 4

The filter assembly used in this example was set up and tested as in Example 3, using an ULTIPOR $N_{66}$® membrane having a microorganism blocking pore rating of about 0.45 micrometers in a housing as generally described in Example 1.

The results were as follows:

| volume (ml) | pressure (psi) | |
|---|---|---|
| 20.0 | 9.3 | induction rate |
| 20.5 | 3.0 | maintenance rate |
| 21.0 | 4.2 | |
| 22.0 | 5.7 | |
| 23.0 | 6.1 | |
| 25 | 6.6 | |
| 30 | 7.6 | |
| 35 | 8.5 | |
| 40 | 9.3 | |
| 45 | 9.9 | |
| 50 | 10.3 | |
| 55 | 10.7 | |
| 60 | 10.9 | |

Examples 3 and 4 demonstrated that a fluid filtration element having a membrane with a microorganism blocking pore rating of about 0.45 micrometers will pass a parenteral emulsion-containing medicament fluid therethrough, but at a higher pressure drop than a similarly tested membrane which has a similar microorganism blocking pore rating but also has a low affinity for amide-group containing materials.

EXAMPLE 5

This Example compared the distribution of lipid particles in filtered DIPRIVAN® to unfiltered DIPRIVAN®. The filter assembly included a LOPRODYNE® membrane having a microorganism blocking pore rating of about 0.45 micrometers as described in Example 3.

A 20 milliliter ampule of DIPRIVAN® was opened, and 5 ml of the emulsion was withdrawn and passed through the filter assembly described above and then through a dynamic light scattering (DLS) device (NICOMP Model 370) for submicron particle size analysis. Another 5 ml of the emulsion was passed through the DLS device without passing it through a filter assembly.

Gaussian analyses revealed the mean diameter of the filtered particles was 202.2 nm (about 0.2 micrometers), while the mean diameter of the unfiltered particles was 223.5 nm (about 0.22 micrometers).

Since comparison of the results showed the mean diameters for the two sets of particles were essentially the same, Example 5 demonstrated that a fluid filtration element having a membrane with a microorganism blocking pore rating of about 0.45 micrometers will pass the lipid emulsion therethrough without adversely affecting the distribution of the lipid particles.

EXAMPLE 6

The fluid filtration element used in this example was formed of five layers of flat discs, each having a nominal diameter of 47 mm and a surface area of about 17.35 $cm^2$ (2.69 $in^2$), which were placed in a jig, as described below. Going from the upstream to the downstream direction, the first three layers were LOPRODYNE® nylon membranes with nominal microorganism blocking pore ratings of 1.2 micrometers, 0.65 micrometers, and 0.45 micrometers, respectively, and each had a CWST of 83 dynes/cm. The next layer was an HDC® microfibrous PBT layer with a pore rating of about 30 micrometers, with the smooth side of the layer facing downstream. The next layer was formed by co-drying two nylon ULTIPOR $N_{66}$® membranes, one having a microorganism blocking pore rating of about 0.2 micrometers and the other having a microorganism blocking pore rating of about 0.8 micrometers, as described in Example 1.

The 5 layers were clamped between the inlet and outlet halves of a housing jig, and the jig was connected to a 0–15 psi gauge, a 60 cc syringe, and a Harvard pump, and tested as generally described in Example 1, although the flow rate was 1.0 ml/min.

Pressure was recorded several times during the test, with the following results:

| volume (ml) | pressure (psi) |
|---|---|
| 5 | 2.1 |
| 6 | 5.6 |
| 7 | 7.0 |
| 10 | 7.2 |
| 14 | 8.0 |
| 15 | 8.3 |
| 17 | 8.9 |
| 20 | 9.7 |

EXAMPLE 7

The fluid filtration element was set up and tested as in Example 6, except that the Harvard pump was programmed to run at a bolus rate of 20.0 ml/min for 20 ml of DIPRIVAN®. The pressure reached 14.9 psi.

Examples 6 and 7 demonstrated that parenteral emulsion-containing medicament fluids may be passed through fluid filtration elements including a number of layers having different pore ratings, and having a coarser pore rating upstream and a finer, bacterial removing (i.e., 0.2 micrometer) pore rating downstream, at a variety of flow rates, including a surge bolus rate, without excessive pressure build up, to produce a bacteria-depleted infusate. Additionally, Examples 6 and 7 demonstrated that parenteral medicament fluids may be passed through fluid filtration elements including layers having different microorganism blocking pore ratings.

EXAMPLE 8

Two filter assemblies as described in Example 3 were challenged with *Moraxella*, in DIPRIVAN®, at flow rates of 20 ml/min and 1.5 ml/min, respectively, using a Sage Instruments Model 351 pump. The input challenge to each assembly was a total of $4.8 \times 10^5$ organisms in each 20 ml of DIPRIVAN®. No organisms were recovered downstream.

Example 8 demonstrated that fluid filtration elements having microorganism blocking pore ratings of about 0.45 micrometers blocked the passage of *Moraxella* without clogging.

EXAMPLE 9

Two filter assemblies as described in Example 3 were tested as generally described in Example 8, at a flow rate 20.0 ml/min, and challenged with *Candida albicans*. The input challenge to each assembly was $0.48 \times 10^4$ cfu/ml$\times$20 ml, which resulted in $9.6 \times 10^5$ total organisms per filter. No organisms were recovered downstream.

Example 9 demonstrated that fluid filtration elements having microorganism blocking pore ratings of about 0.45 micrometers blocked the passage of *Candida albicans* without clogging.

EXAMPLE 10

Two filter assemblies as described in Example 3 were tested as generally described in Example 8, at a flow rate of 20.0 ml/min, and challenged with *Acinetobacter lwoffi* in 20 ml of DIPRIVAN® containing either $4.8 \times 10^5$ or $5.3 \times 10^5$ total organisms. No organisms were recovered downstream.

Example 10 demonstrated that fluid filtration elements having microorganism blocking pore ratings of about 0.45 micrometers blocked the passage of *Acinetobacter lwoffi* without clogging.

EXAMPLE 11

Two filter assemblies similar to those described in Example 1, each having a fluid filtration element formed from ULTIPOR N$_{66}$® membranes and having a microorganism blocking pore rating of about 0.2 micrometers, were tested as generally described in Example 8, at a flow rate of 20.0 ml/min, and challenged with *Acinetobacter lwoffi* in 20 ml of DIPRIVAN® containing $8.8 \times 10^4$ total organisms.

The filter assemblies allowed 3.5 ml of fluid to pass prior to pump failure unrelated to the function of the filter assembly. No organisms were recovered downstream.

Example 11 demonstrated that fluid filtration elements having microorganism blocking pore ratings of about 0.2 micrometers at least provide initial blockage of *Acinetobacter lwoffi*.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for treating a parenteral emulsion-containing medicament fluid comprising:

passing a parenteral emulsion-containing medicament fluid comprising an anesthetic through a microorganism blocking porous fluid filtration element and intravascularly administering the fluid to a patient.

2. The method of claim 1 comprising passing the parenteral emulsion-containing medicament fluid comprising an anesthetic through the fluid filtration element wherein said element has a pore rating of less than about 0.8 micrometers.

3. The method of claim 1 comprising passing the parenteral emulsion-containing medicament fluid comprising an anesthetic through the fluid filtration element wherein said element has a pore rating of less than about 0.5 micrometers.

4. The method of claim 2 wherein the parenteral emulsion-containing fluid comprising an anesthetic includes an oil-in-water emulsion.

5. The method of claim 1 wherein passing the fluid through the fluid filtration element comprises passing the parenteral emulsion-containing medicament fluid comprising an anesthetic through a device including a housing having an inlet and an outlet and defining a parenteral emulsion-containing medicament fluid comprising an anesthetic flow path between the inlet and the outlet, wherein the fluid filtration element is arranged between the inlet and the outlet and across the parenteral emulsion-containing medicament fluid flow path.

6. The method of claim 5 further comprising separating a gas from the fluid flow path of the parenteral emulsion-containing medicament fluid.

7. The method of claim 6 wherein passing the gas from the fluid flow path of the parenteral emulsion-containing medicament fluid comprises passing the gas through at least one gas venting element.

8. The method of claim 1 wherein passing the parenteral emulsion-containing medicament fluid through the microorganism blocking fluid filtration element depletes the fluid of at least one of *Candida albicans*, *Acinetobacter lwoffi*, and *Moraxella*.

9. The method of claim 1 wherein the parental emulsion-containing medicament fluid comprising an anesthetic includes a lipid.

10. A method for treating a parenteral emulsion-containing medicament fluid comprising:

passing a parenteral emulsion-containing medicament fluid comprising propofol through a microorganism blocking fluid filtration element.

11. The method of claim 10 comprising passing the parenteral emulsion-containing medicament comprising propofol fluid through the fluid filtration element wherein said element has a pore rating of less than about 0.5 micrometers.

12. The method of claim 10 wherein passing the parenteral emulsion-containing medicament comprising propofol fluid through the fluid filtration element comprises passing the fluid through a device including a housing having an inlet and an outlet and defining a parenteral emulsion-containing medicament fluid flow path between the inlet and the outlet, wherein the fluid filtration element is arranged between the inlet and the outlet and across the parenteral emulsion-containing medicament fluid flow path.

13. The method claim 12 further comprising separating a gas from the fluid flow path of the parenteral emulsion-containing medicament fluid.

14. The method of claim 13 wherein passing the gas from the flow path of the parenteral emulsion-containing medicament fluid comprises passing the gas through at least one gas venting element.

15. The method of claim 12 further comprising administering the parenteral emulsion-containing medicament fluid to a patient.

16. The method of claim 10 comprising passing propofol through the fluid filtration element which comprises two or more layers.

17. The method of claim 16 comprising passing propofol through two or more layers having a pore rating of less than about 0.8 micrometers.

18. The method of claim 17 wherein passing the propofol through two or more layers includes passing the propofol through at least one layer having a pore rating of about 0.45 micrometers.

19. The method of claim 10 wherein the fluid filtration element comprises at least an upstream layer, and a downstream microorganism blocking layer, the method comprising passing propofol through the upstream layer and the downstream microorganism blocking layer.

20. The method of claim 19 comprising passing propofol through the upstream layer having a pore rating in the range of about 5 to about 1 micrometers.

21. The method of claim 20 comprising passing propofol through the downstream layer having a pore rating in the range of about 0.8 to about 0.2 micrometers.

22. The method of claim 21 comprising passing propofol through the downstream layer having a pore rating of about 0.45 micrometers.

23. The method of claim 10 wherein passing the parenteral emulsion-containing medicament fluid through the microorganism blocking fluid filtration element depletes the fluid of at least one of *Candida albicans, Acinetobacter lwoffi,* and *Moraxella.*

* * * * *